(12) United States Patent
Shon

(10) Patent No.: US 6,835,920 B2
(45) Date of Patent: Dec. 28, 2004

(54) MICROWAVE OVEN

(75) Inventor: Jong-Chull Shon, Suwon (KR)

(73) Assignee: Samsung Electronics Co., LTD, Suwon-si (KR)

(*) Notice: Subject to any disclaimer, the term of this patent is extended or adjusted under 35 U.S.C. 154(b) by 44 days.

(21) Appl. No.: 10/005,312

(22) Filed: Dec. 7, 2001

(65) Prior Publication Data
US 2003/0029864 A1 Feb. 13, 2003

(30) Foreign Application Priority Data
Aug. 7, 2001 (KR) ................ 10-2001-0047535

(51) Int. Cl.⁷ ................................ H05B 6/50
(52) U.S. Cl. ................ 219/707; 219/702; 338/35
(58) Field of Search ................ 219/707, 705, 219/702, 716, 704, 703, 715, 718, 719, 757; 99/325; 73/1.07, 1.02, 19.01, 24.04, 73, 25.03; 338/308, 34, 314, 73, 309, 35; 252/519.5, 519.54; 422/105; 324/703, 606

(56) References Cited
U.S. PATENT DOCUMENTS

| | | | |
|---|---|---|---|
| 4,015,230 A | * | 3/1977 | Nitta et al. ............ 338/35 |
| 4,080,564 A | | 3/1978 | Nitta et al. |
| 4,422,129 A | | 12/1983 | Briant et al. |
| 4,501,147 A | | 2/1985 | Niwa |
| 4,520,341 A | * | 5/1985 | Miyoshi et al. ........ 338/35 |
| 4,677,415 A | | 6/1987 | Howng |
| 4,707,244 A | * | 11/1987 | Harman et al. ........ 204/430 |
| 5,837,886 A | * | 11/1998 | Nakahara et al. ...... 73/31.06 |

* cited by examiner

Primary Examiner—Quang T. Van
(74) Attorney, Agent, or Firm—Staas & Halsey LLP (57) ABSTRACT

A microwave oven includes a magnetron to generate microwaves and a cooking chamber to contain food to be cooked using the generated microwaves. The microwave oven further includes a humidity detector to detect moisture formed from the food being cooked. The humidity detector is provided at air outlets of the cooking chamber, and includes first and second electrodes formed on a board to be space apart from each other at a predetermined interval to form a gap therebetween. The control unit of the microwave oven controls the cooking operation of the microwave oven according to the output of the humidity detector.

38 Claims, 10 Drawing Sheets

(PRIOR ART)

FIG. 10

MICROWAVE OVEN

CROSS-REFERENCE TO RELATED APPLICATIONS

This application claims the benefit of Korean Application No. 200147535, filed Aug. 7, 2001 in the Korean Industrial Property Office, the disclosure of which is incorporated herein by reference.

BACKGROUND OF THE INVENTION

1. Field of the Invention

The present invention relates generally to microwave ovens, and more particularly, to a microwave oven with a humidity detector that has a simple construction and is inexpensively fabricated.

2. Description of the Prior Art

In general, microwave ovens are apparatuses that cook food using microwaves. In a conventional microwave oven, the intensity of microwaves and the cooking time are determined according to a state of food to be cooked. The material, shape and the kind of the food placed in the cooking chamber of the microwave oven determines the absorption of the microwaves and the amount of energy required. As such, the microwave oven detects and assesses the state of the food being cooked using a variety of sensors. Based upon the assessed state, the microwave oven and care out a cooking operation.

Figure 9:
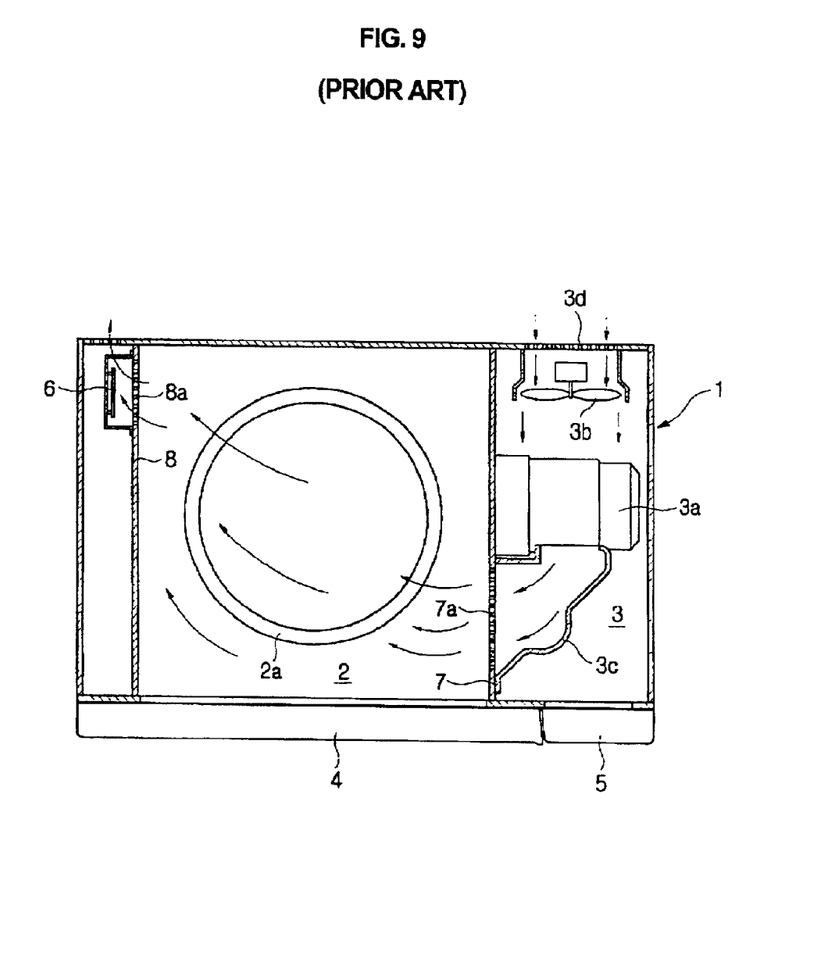
FIG. 9 is a partial sectional view showing a conventional microwave oven.

As shown in FIG. 9, a conventional microwave oven comprises a body 1, the interior of which is partitioned into a cooking cavity 2 and a machine room 3. A door 4 is hinged to the body 1 so as to close the cooking cavity 2. The microwave oven also has a control panel 5, which is installed at the front wall of the body 1 and is provided with a variety of control buttons. A humidity sensor 6 is installed in the body 1 to sense the operational conditions of the food in the cooking cavity 2.

The cooking cavity 2 has an opening in front, and has a turntable cooking tray 2a rotatably mounted on a bottom of the cooking cavity 2. An air inlet 7a is formed at a front portion of a sidewall 7 of the cooking cavity 2 so as to allow the cooking cavity 2 to communicate with the machine room 3. Air flows from the machine room 3 into the cooking cavity 2 through the air inlet 7a. An air outlet 8a is formed at a rear portion of the opposite sidewall 8 of the cooking cavity 2 so as to discharge the air from the cooking cavity 2 to the atmosphere exterior to the microwave oven.

A magnetron 3a, a cooling fan 3b, an air guide duct 3c, and other similar devices (not shown) are installed within the machine room 3. The magnetron 3a generates the high-frequency electromagnetic waves, while the cooling fan 3b sucks atmospheric air into the machine room 3 to cool the elements 3a, 3b installed within the machine room 3. The air guide duct 3c guides the air inside the machine room 3 to the air inlet 7a and into the coking cavity 2. The cooling fan 3b is installed between the magnetron 3a and a rear wall of the machine room 3. In order to allow the atmospheric air to flow into the machine room 3, a predetermined area of the rear wall of the machine room 3 is perforated to form a plurality of air suction holes 3d.

The humidity sensor 6 is installed on a sidewall 8 of the cooking cavity 2 at a position adjacent to an air outlet 8a. Thus, the humidity sensor 6 is located. In an air discharging passage leading from the cooking cavity 2. The humidity sensor 6 thus senses the humidity of the exhaust air discharged from the cooking cavity 2 through the air outlet 8a and that is defined by a surface of the humidity sensor 6. The humidity sensor 6 is connected to a circuit board (not shown) installed in the control panel 5, and outputs a signal to the circuit board.

When turning on the microwave oven containing food on the cooking tray 2a, the high frequency electromagnetic waves are radiated from the magnetron 3a into the cooking cavity 2 and the food is cooked using the generated electromagnetic waves.

During such an operation of the microwave oven the cooling fan 3b is rotated to form a suction force to suck the atmospheric air into the machine room 3 through the air suction holes 3d as to cool the elements installed in the room 3. The air is, thereafter guided to the air inlet 7a by the air guide duct 3c and introduced into the cooking cavity 2 through the air inlet 7a. The air inside the cooking cavity 2 is exhausted along with vapor (moisture) generated from the food, which is exhausted in the form of humidity to the atmosphere through the air outlet 8a as shown by the arrows of FIG. 9. Therefore, it is possible to remove odor and vapor generated from food during the operation of the oven. When the exhaust air from the cooking cavity 2 to the atmosphere, it comes into contact with and is turned by the humidity sensor 6. The humidity sensor 6 senses the humidity of the exhaust air, and outputs a signal to the circuit board of the control panel 5. The circuit board of the control panel 5 controls the operation of the magnetron 3a, the cooking tray 2a and the cooling fan 3b in response to the signal from the humidity sensor 6, thus automatically cooks the food on the tray 2a.

The conventional microwave oven shown in FIG. 9 uses the humidity sensor 6 to detect the cooking state of the food. The conventional microwave oven detects the moisture formed from the food in the form of humidity, and controls the cooking operation according to the detected moisture.

The conventional humidity sensor 6 is a porous humidity sensor made of a semiconductor ceramic of $MgCrO_4$—$TiO_2$. The conventional semiconductor ceramic humidity sensor 6 has a characteristic in that its value of resistance is varied according to the amount of moisture that infiltrates into the pores/holes of the semiconductor ceramic humidity sensor 6.

However, the conventional semiconductor ceramic humidity sensor 6 is disadvantageous in that its fabrication cost is high. In addition, when remainders exist in the holes, the detection performance deteriorates and the overall life span of the sensor 6 is shortened.

SUMMARY OF THE INVENTION

Accordingly, to solve the above and other problems, an object of the present invention is to provide a microwave oven with a humidity detector that has a simple construction and is inexpensively fabricated.

Additional objects and advantages of the invention will be set forth in part in the description which follows and, in part, will be obvious from the description, or may be learned by practice of the invention.

In order to accomplish the above and other objects, a microwave oven according to an embodiment of the invention includes a magnetron to generate microwaves, a cooking chamber to contain food to be cooked using the generated microwaves, a humidity detector to detect humidity formed as the food is being cooked, the humidity detector being provided at an outlet of the cooking chamber to receive air containing moisture from the cooking chamber and including first and second electrodes formed on a board and spaced apart from each other at a predetermined interval to form a gap therebetween into which the air is received, and a control unit to control the cooking operation of the microwave oven according to an output of the humidity detector.

BRIEF DESCRIPTION OF THE DRAWINGS

The above and other objects, features and other advantages of the present invention will be more clearly understood and more readily appreciated from the following detailed description of the embodiments taken in conjunction with the accompanying drawings, in which.

DESCRIPTION OF THE PREFERRED EMBODIMENTS

Hereinafter, a microwave oven in accordance with the embodiments of the present invention is described in detail, examples of which are illustrated with reference to the accompanying drawings, wherein like reference numerals refer to the like elements throughout. The embodiments are described below in order to explain the present invention by referring to the figures.

Figure 1:
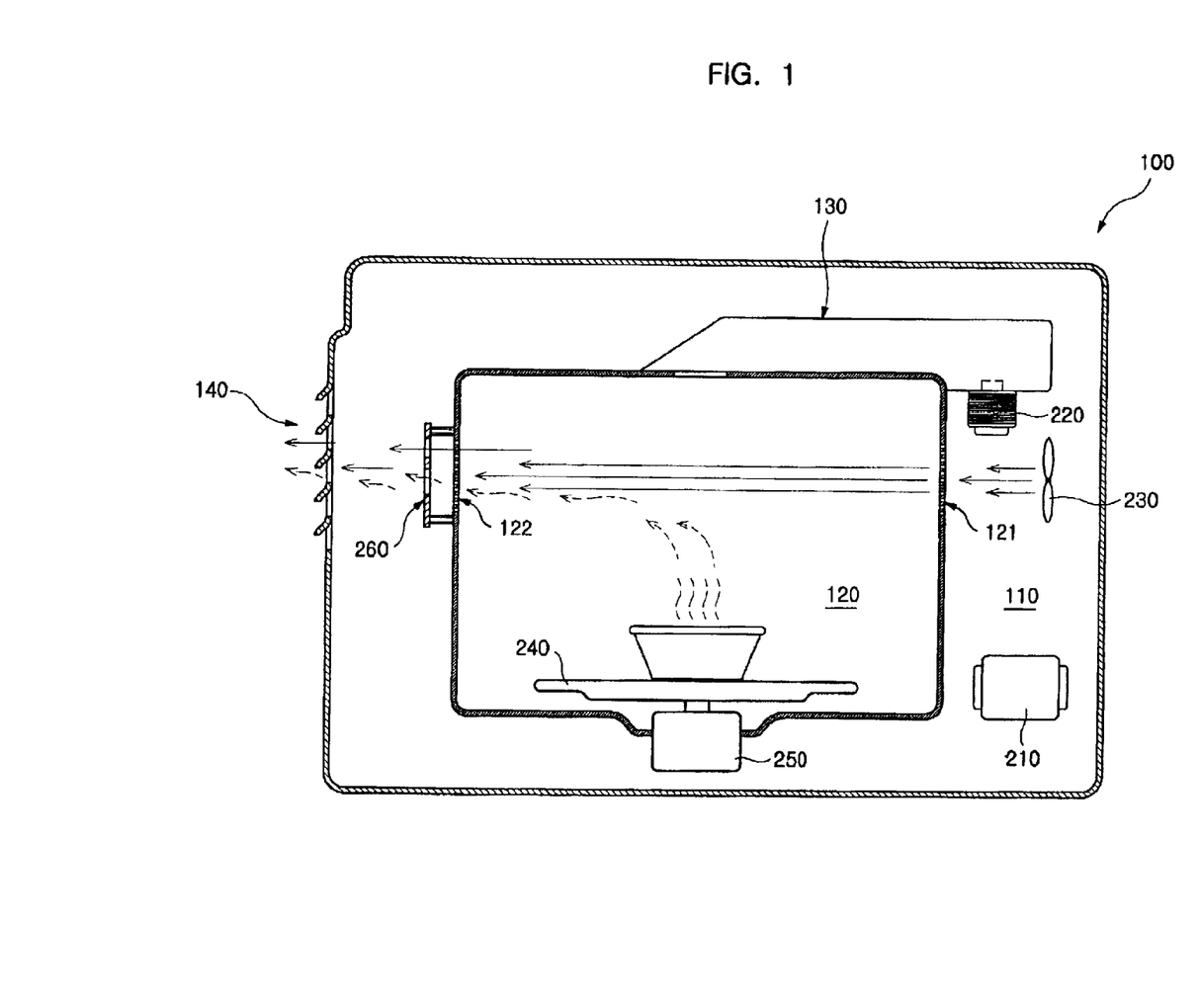
FIG. 1 is a partial sectional view showing a microwave oven in accordance with an embodiment of the present invention.

FIG. 1 is a partial sectional view showing a microwave oven in accordance with an embodiment the present invention. Referring to FIG. 1, an oven body 100 is provided with a cooking chamber 120 and an electric device chamber 110. A high-voltage transformer 210, a magnetron 220, and an air circulation fan 230 are located in the electric device chamber 110. Additionally, the oven body 100 is provided with a wave guide 130 that transmits microwaves generated in the magnetron 220 to the cooking chamber 120. While not shown, it is understood that additional devices can be located in the electric device chamber 110.

A tray 240 to hold the food to be cooked and a tray motor 250 to rotate the tray 240 are placed in the cooking chamber 120. Air inlets 121 are formed on one side of the wall of the cooking chamber 120 to allow air circulated by the fan 230 to enter the cooking chamber 120. Air outlets 122 are formed on another side of the wall of the cooking chamber 120 to allow air having entered the cooking chamber 120 through the air inlets 121 to be discharged from the cooking chamber 120. A humidity detector 260 is mounted on the outside of the wall of the cooking chamber 120 opposite the air outlets 122. It is understood that the tray 240 and the tray motor 250 need not be present in all circumstances. Further it is understood that ones of the air outlets 122 may be disposed on additional walls.

Figure 2:
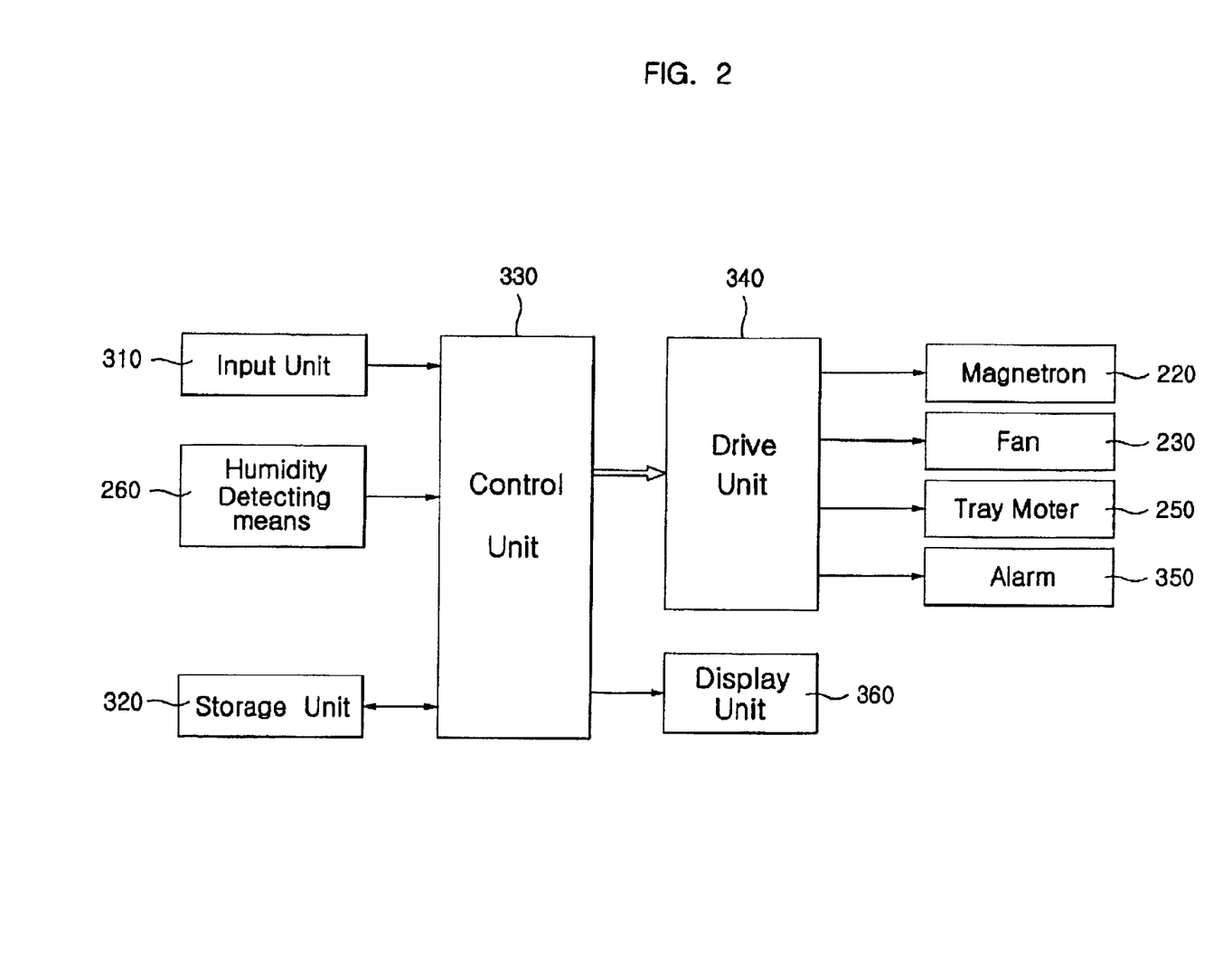
FIG. 2 is a block diagram of the microwave oven according to another embodiment of the present invention.

FIG. 2 is a block diagram of the microwave oven of an embodiment of present invention as well as the humidity detector 260. Referring to FIG. 2, the microwave oven has a control unit 330 to control an overall operation of the microwave oven. The control unit 330 may be a general or special purpose computer, depending on the circumstances. An input unit 310 to receive cooking commands from a user and which is in communication with the control unit 330. The humidity detector 260 is in communication with the control unit 330. A storage unit 320 to store operating software and cooking information data is in communication with the control unit 330.

In addition, a drive unit 340 is used to operate the magnetron 220, the fan 230, the tray motor 250 and an alarm 350, which auditory informs a user of the operation of the microwave oven. The drive unit 340 is in communication with the control unit 330. A display unit 360 is in communication with the control unit 330 and is controlled by the control unit 330. It is understood that additional elements may be added or ones of the shown elements may be removed according to a desired functionality of the microwave oven.

Figure 3:
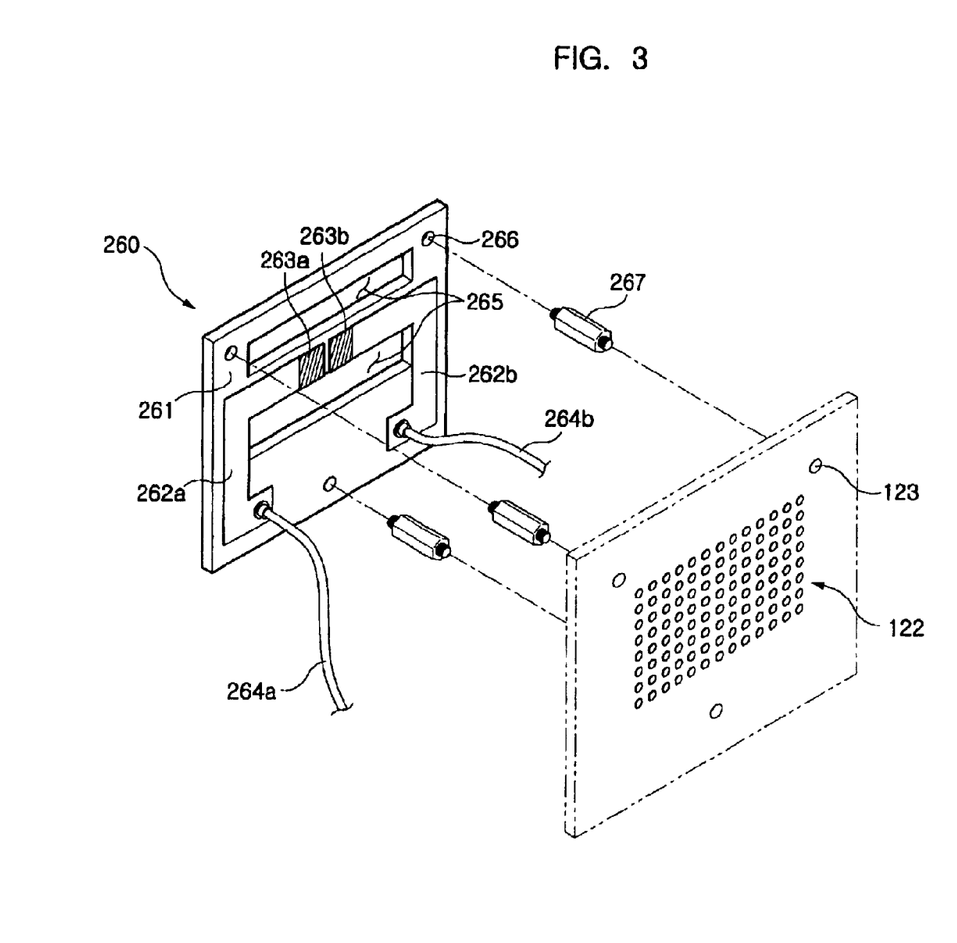
FIG. 3 is a perspective view showing a humidity detector in accordance with yet another an embodiment of the present invention.

FIG. 3 is a perspective view showing humidity detector 260 in accordance with an embodiment of the present invention. Referring to FIG. 3, a first electrode 262a and a second electrode 262b are formed on a non-conductive board 261, such as a printed circuit board (PCB) or a PCB having a coating such as a ceramic coating and/or a polymer coating.

The electrodes 262a, 262b are of copper, gold, or other conductive material. The first and second electrodes 262a and 262b are spaced apart from each other by a certain distance to form a gap therebetween. The gap is shown as less than of equal to 0.18 mm, but may be wider up to 0.25 mm according to a desired resistance of the humidity detector 260. The air outlet from the cooking chamber 120 is deflected at the board 261 within the gap, wherein the moisture content of the air changes a resistance between the electrodes 262a, 262b indicating a content of the moisture in the air.

Figure 10:
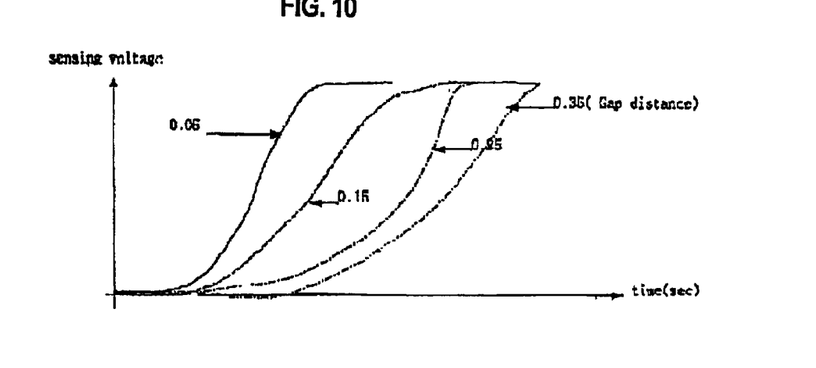
FIG. 10 is a graph showing the effect of gap distances on sensing voltages according to embodiments of the present invention.

As shown in FIG. 10, at a gap distance of 0.05 mm, the humidity detector 260 becomes susceptible to sudden changes in sensing values and is thus too sensitive for the purposes of cooking food in a microwave oven. In contrast, for a gap distance of 0.25 mm or greater, the humidity detector 260 is not sensitive enough for the purposes of cooking food in a microwave oven. However for gap distances between 0.05 mm and 0.25 mm, the humidity detector 260 is better suited for cooking food in a microwave oven. According to an embodiment of the invention, the gap is 0.15 mm. However, it is understood that other gap distances can be used in microwave ovens, and that the gap distances can be varied based on uses other than in microwave ovens according to a desired sensitivity and other factors.

A first detection electrode 263a is formed by plating one end of the first electrode 262a sequentially with nickel and gold so as to prevent oxidation due to moisture. A first wire 264a is attached to the other end of the first electrode 262a connect the first electrode 262a with the another device/element (not shown). Similarly, a second detection electrode 263b is formed by plating one end of the second electrode 262b sequentially with nickel and gold so as to prevent oxidation due to moisture. A second we 264b is connected to the other end of the second electrode 262a so as to connect the second electrode 262b with another device/element (not shown). However, it is understood that other types of materials can be used for the board 261, electrodes 262a, 262b and the detection electrodes 263a, 263b.

Two detection slits 265 are formed above and below the first and second electrodes 262a and 262b to allow air discharged through the air outlets 122 to pass through. The detecting slits 265 have an area equal to or greater than twice the area of the first and second detecting electrodes 263a and 263b. The detection slits 265 need not be used in all circumstances.

Attaching holes 266 are formed to attach the humidity detector 260 to a wall of the cooking chamber 120. The humidity detector 260 is attached to the wall of the cooking chamber 120 with a plurality of spacers 267 inserted into the attaching holes 266 and a plurality of attaching holes 123 formed in the wall of the cooking chamber 120.

Figure 4:
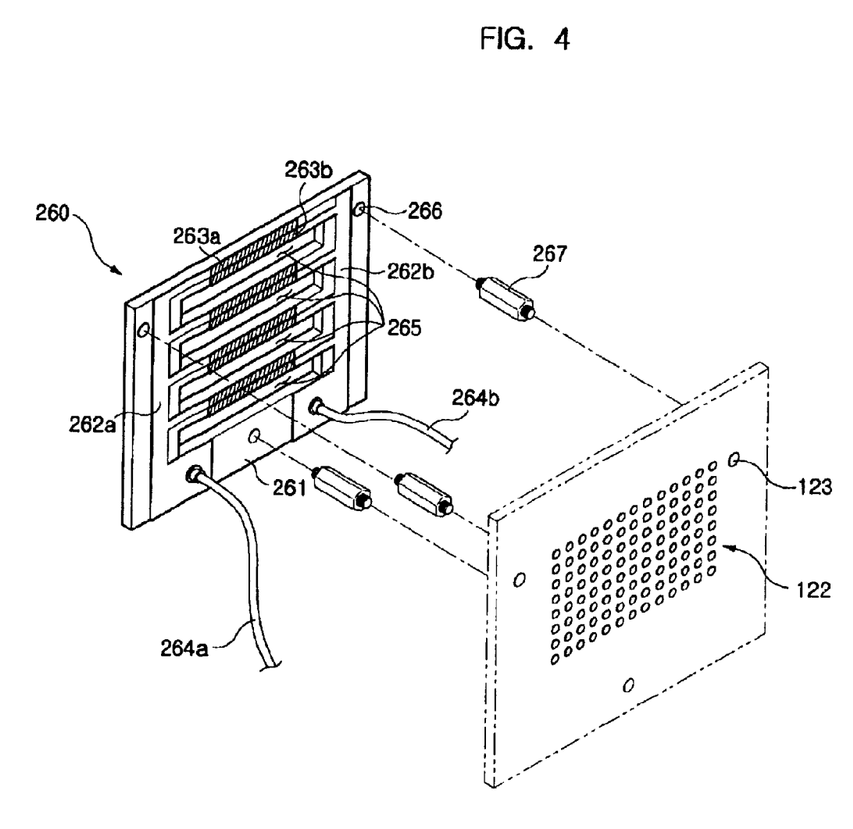
FIG. 4 is a perspective view showing a humidity detector in accordance with still another embodiment of the present invention.

FIG. 4 is a perspective view showing a humidity detector 260 in accordance with another embodiment of the present invention. Referring to FIG. 4, the first and second electrodes 262a and 262b are provided in the form of interlocked combs by having multiple pairs of first and second detecting electrodes 263a and 236b such that the first and second detecting electrodes 263a and 263b are provided in the form of lines. The other construction of the humidity detector 260 is otherwise the same as the corresponding construction of the humidity detector of FIG. 3. The use of multiple pairs of detecting electrodes 263a, 263b increases a sensitivity of the humidity detector 260.

Figure 5:
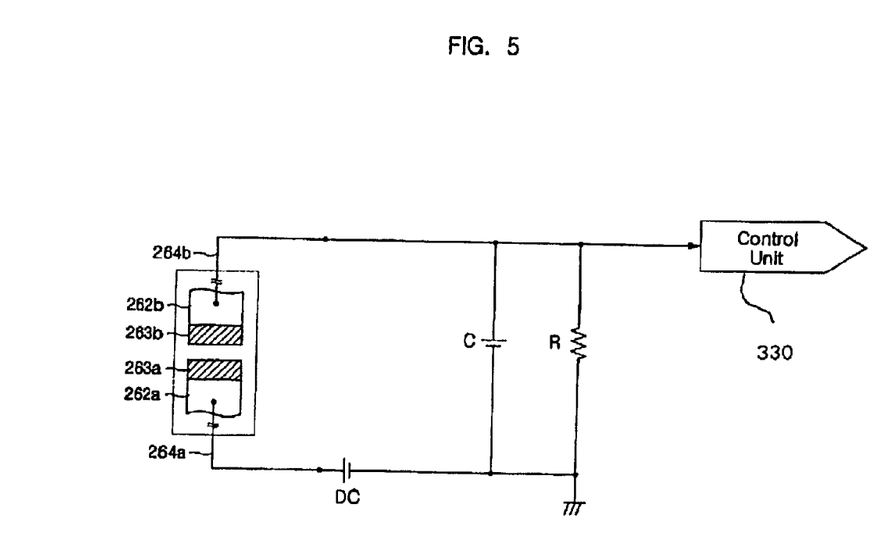
FIG. 5 is a circuit diagram of a humidity detector in accordance with yet still another embodiment of the present invention.

FIG. 5 is a circuit diagram of a humidity detector 260 in accordance with an embodiment of the present invention. Referring to FIG. 5, the first wire 264a is connected to the first electrode 262a and to the anode of a direct current source DC of 5 volts. The cathode of the direct current source DC is grounded. The second wire 264b is connected to the second electrode 262b and to the control unit 330. A resistor R and a capacitor C are each connected in parallel with the second wire 264b and the ground. The resistor R has a value ranging 200 to 500 kΩ, but can be varied depending on a voltage of the direct current source DC. It is understood that the connection directions of the first and second wires 264a and 264b respectively connected to the first and second electrodes 262a and 262b may be changed with each other.

Figure 6:
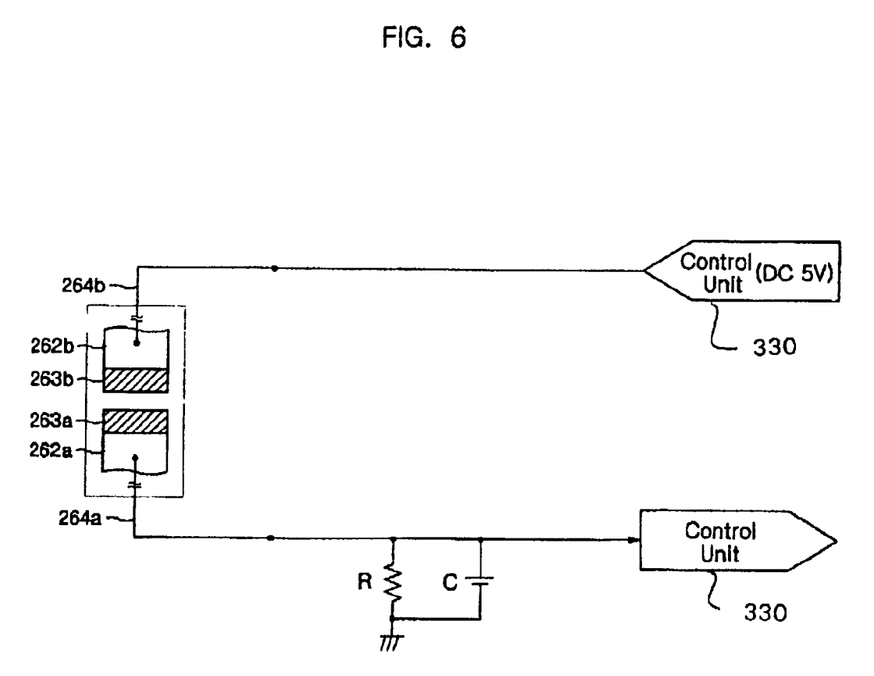
FIG. 6 is a circuit diagram of a humidity detector in accordance with a further embodiment of the present invention.

FIG. 6 is a circuit diagram of a humidity detector 260 in accordance with another embodiment of the present invention. Referring to FIG. 6, there is no separate direct current source DC provided which is applied to the humidity detector 260. Instead, a direct current voltage of about 5 volts is supplied to the second electrode 262b through the second wire 264b from the control unit 330. The first electrode 262a is connected to the control unit 330 through the first wire 264a. A resistor R and a capacitor C are each connected in parallel with the first wire 264a and the ground. The resistor R has a value ranging 200 to 500 Ωk, but can be varied depending on the direct current voltage. It is understood that the connection directions of the first and second wires 264a and 264b respectively connected to the first and second electrode 262a and 262b may be changed with each other.

In the humidity detector 260, the resistance between the first and second detecting electrodes 263a and 263b is determined by the cross section of and the length between the first and second detecting electrodes 263a and 263b. In the shown embodiment, the length is constant, so the resistance only depends on the cross section of the fist and second detecting electrodes 263a and 263b. If a moisture or gas does not remain in the space between the first and second detecting electrodes 263a and 263b, the value of the resistance becomes infinite, thus forming an open circuit. If the moisture or gas remains in the space between the first and second detecting electrodes 263a and 263b, the value of the resistance is reduced, thereby allowing a current to flow between the first and second detecting electrodes 263a and 263b. The amount of the current reflects a moisture content of the air received between the detecting electrodes 263a, 263b.

Figure 7:
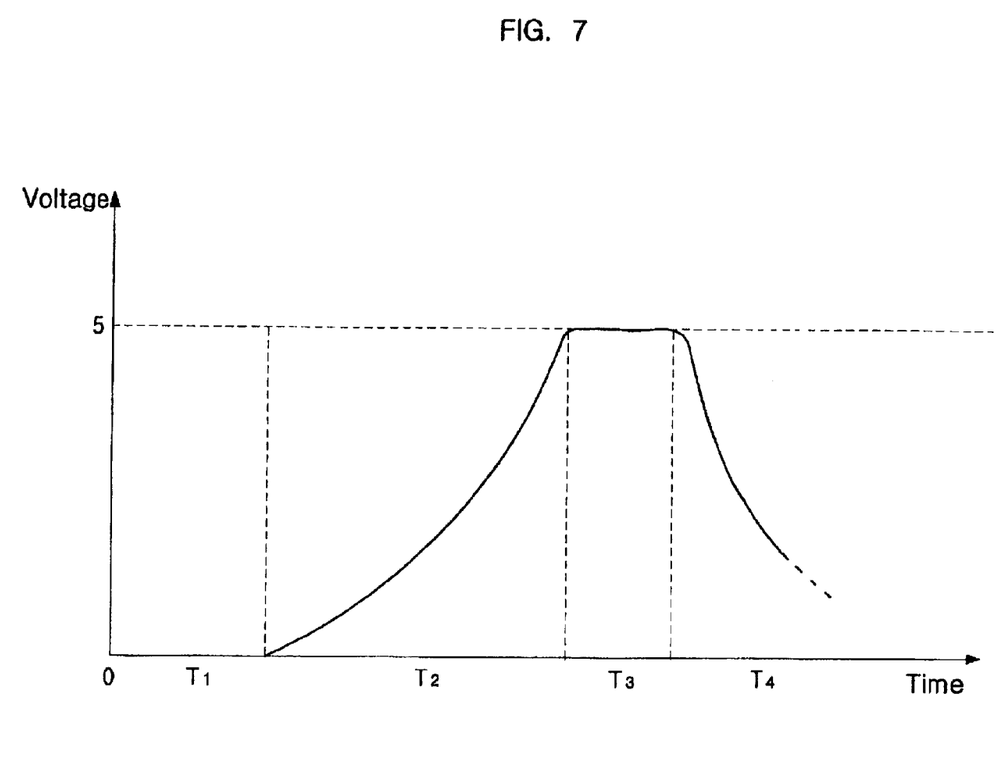
FIG. 7 is a graph showing a cooking state determination according to the detection results of a yet further embodiment of the humidity detector of the present invention.

FIG. 7 is a graph showing the coking state determination according to the detection results of the humidity detector 260 of the present invention. Referring to FIG. 7, when a cooking operation is initiated, the food is heated by the microwaves generated by the magnetron 220. Moisture formed while heating the food is detected by the humidity detector 260. In this case, the heating time of the microwave oven is varied depending on the amount of foods. The load according to the amount of food is determined by measuring a first time period T1, during which no moisture was formed after the initiation of the cooking operation (i.e., the humidity detector 260 does not produce a voltage).

When a certain time period according to the amount of food (the first time period T1), elapses, the formation of moisture from the food begins and the amount of moisture in the air output from the cooking chamber 120 increases. The moisture or gas remains on the board 261 in the space between the first and second detecting electrodes 263a and 283b of the humidity detector 260. Accordingly, the resistance between the first and second detecting electrodes 263a and 263b is reduced, thereby increasing the output voltage of the humidity detector 260. Thus, the output voltage of the humidity detector 260 gradually increases to reach the voltage provided of the direct current source DC. When the output voltage of the humidity detector 260 equals the voltage provided by the direct current source DC, the food has reached its boiling point. The time period between which the output voltage of the humidity detector 260 has reached the voltage of the direct current source DC and when the formation of moisture begins is a second time period T2.

When the food reaches its boiling point, the output voltage of the humidity detector 260 remains constant. In the shown embodiment, the voltage would be 5 Volts, which is the voltage of the direct current source DC. The third time period T3, during which the output voltage of the humidity detector 260 remaining constant, varies depending on the amount of food and the amount of the moisture contained in the food. Accordingly, the amount of the moisture contained in the food can be determined by measuring the third time period T3.

When the third time period T3 elapses, the amount of the moisture is considerably reduced, while the resistance between the first and second detecting electrodes 263a and 263b correspondingly increases. Accordingly, the output voltage of the humidity detector 260 is reduced. The time period for which the output voltage has been reduced is a fourth time period T4. The drying time period of the food can be determined by measuring the fourth time period T4.

The cooking state determination data according to the first to fourth time period T1 to T4 are stored in the storage unit 320 for various foods. The storage unit 320 can be updated to account for new foods and refined cooking techniques using portable storage media or through a network connection such as through the internet.

Hereinafter, the operation of the microwave oven of the present invention is described with reference to FIG. 8, which is a flowchart showing the operation of the microwave oven according to an embodiment of the present invention. It is understood that the operation can be performed using a computer program encoded on a computer readable medium and executed by a computer.

Figure 8:
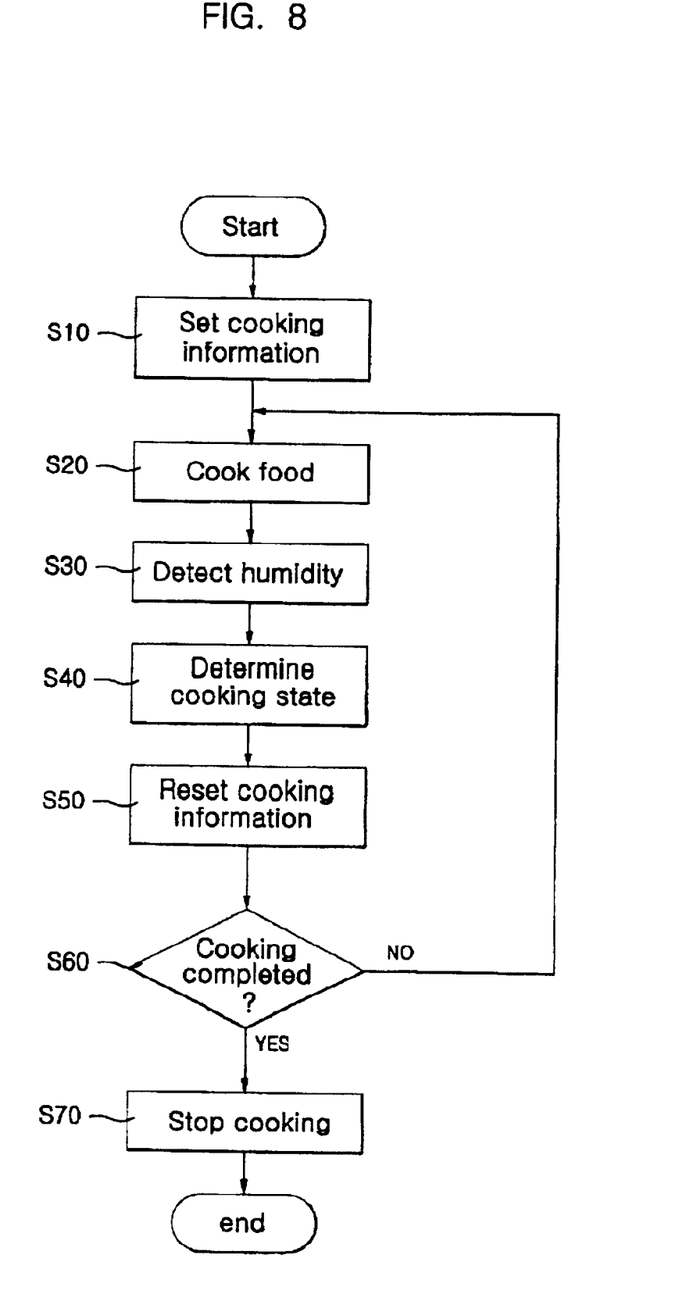
FIG. 8 is a flowchart showing the operation of the microwave oven according to a still further embodiment of the present invention.

Referring to FIG. 8, the control unit 330 automatically or manually sets the cooking information so as to cook the food (S10). In order to set the cooking information, a user inputs an automatic cooking command, or directly inputs the cooking information through the input unit 310. The input unit 310 transmits a signal corresponding to the information provided by the user to the control unit 330. The control unit 330 automatically or manually sets the cooking information in response to the signal transmitted from the input unit 310.

After the cooking information is set, the control unit 330 starts the cooking operation through the drive unit 340, which operates the magnetron 220, the tray motor 250, the fan 230, and any other similar devices (S20). Additionally the control unit 330 controls the display unit 360 to display a variety of messages related to the cooking operation.

When the cooking operation is started, the control unit 330 detects the humidity (S30) in the air from the cooking chamber 120 using the humidity detector 260. The control unit 330 converts a voltage signal transmitted from the humidity detector 260 into a digital signal, and detects the humidity according to the value of the digital signal.

The control unit 330 determines the cooking state of the food according to the value of humidity detected by the humidity detector 260 at the step S30 (S40). Specifically, the control unit 330 determines the cooking state of the food according to the cooking state determination data set in advance (i.e., based upon known values for $T_1$, $T_2$, $T_3$ and/or $T_4$). The control unit 330 resets the cooking information, such as the cooking time and an amount of cooking electricity, according to the cooking state determined at the step S40 (S50).

Thereafter, the control unit 330 determines whether the cooking operation is completed (S60). If the cooking operation is not completed because a cooking time has not elapsed, the control unit 300 continues the cooking operation. If the cooking operation is completed because the cooking time elapses, the control unit 300 controls the drive unit 340 to stop the operation of the magnetron 220, the tray motor 250 and the fan 230, thus stopping the cooking operation (S70).

As described above, the present invention provides a microwave oven with a humidity detector, which has simple construction, so the humidity detector can be easily and inexpensively fabricated with a superior reliability. However, it is understood that the humidity detector according to the present invention could be used with other appliances such as convection ovens or other heating devices, in air conditioning systems such as in HVAC or humidifying systems, or in any application where humidity needs to be detected.

Although the preferred embodiments of the present invention have been disclosed for illustrative purposes, those skilled in the art will appreciate that various modifications, additions and substitutions are possible, without departing from the scope and spirit of the invention as recited in the accompanying claims and equivalents thereof.

What is claimed is:

1. A sensor to sense a liquid content in a gas, comprising:
   a board;
   a first electrode disposed on said board; and
   a second electrode disposed on said board opposite said first electrode to form a gap therebetween,
   wherein:
   the gas is received into the gap such that the liquid forms a conductive path between said first and second electrodes as to vary a resistance across the gap,
   a bottom portion of the gap exposed to the gas comprises a non-conductive material, and
   said board comprises vents through which portions of the gas not received within the gap pass.

2. The sensor of claim 1, further comprising a non-conductive layer of the non-conductive material to form the bottom of the gap and which extends between sidewalls of the first and second electrodes.

3. The sensor of claim 2, wherein the nonconductive layer comprises one of a ceramic or polymer layer.

4. The sensor of claim 2, wherein said board comprises the non-conductive layer, and the liquid is deposited on said board so as to vary a resistance between said first and second electrodes.

5. The sensor of claim 2, wherein said board comprises a printed circuit board.

6. The sensor of claim 1, where said first and second electrodes further comprise first and second detection portions forming side walls of the gap.

7. The sensor of claim 6, wherein an amount of resistance between said first and second electrodes across the gap corresponds to cross sectional areas of the side walls exposed to the gas in the gap.

8. The sensor of claim 6, wherein a distance between the first and second detection portions is constant.

9. The sensor of claim 6, wherein an amount of resistance corresponds to an amount of the liquid in the gap, cross sectional areas of the side walls exposed to the gap, and a distance between the first and second detection portions across the gap.

10. The sensor of claim 6, wherein one of the first and second detection portions further comprise the protective layer to prevent corrosion due to the liquid.

11. The sensor of claim 10, wherein the protective layer comprises a layer of gold and a layer of nickel.

12. The sensor of claim 1, wherein:
    said first electrode comprises first detection portions extending adjacent to each other, and
    said second electrode comprises second detection portions, each of the second detection portions extending adjacent to a corresponding one of the first detection portions to define a corresponding gap therebetween.

13. The sensor of claim 12, wherein a non-conductive layer defines bottom surfaces to the corresponding gaps.

14. The sensor of claim 1, wherein a distance between the first and second detection portions is at or between 0.5 mm and 0.25 mm.

15. The sensor of claim 14, wherein a distance between the first and second detection portions is substantially 0.15 mm.

16. A sensor to sense a liquid content in a gas, comprising:
    a board;
    a first electrode disposed on said board; and
    a second electrode disposed on said board opposite said first electrode to form a gap there between, wherein:
the gas is received into the gap such that the liquid forms a conductive path between said first and second electrodes as to vary a resistance across the gap, and
said board comprises vents through which portions of the gas not received within the gap pass.

17. The sensor of claim 16, further comprising a non-conductive layer to form a bottom of the gap and which extends between sidewalls of the first and second electrodes.

18. The sensor of claim 17, wherein the non-conductive layer comprises one of a ceramic or polymer layer.

19. The sensor of claim 17, wherein said board comprises the non-conductive layer, and the liquid is deposited on said board so as to vary a resistance between said first and second electrodes.

20. The sensor of claim 18, wherein said board comprises a printed circuit board.

21. The sensor of claim 16, where said first and second electrodes further comprise first and second detection portions forming side walls of the gap.

22. The sensor of claim 21, wherein an amount of resistance between said first and second electrodes across the gap corresponds to cross sectional areas of the side walls exposed to the gas in the gap.

23. The sensor of claim 21, wherein a distance between the first and second detection portions is constant.

24. The sensor of claim 16, wherein a distance between the first and second detection portions is at or between 0.5 mm and 0.25 mm.

25. The sensor of claim 16, wherein a distance between the first and second detection portions is substantially 0.15 mm.

26. The sensor of claim 16, wherein said first and second electrodes further comprise first and second detection portions forming side walls of the gap, and one of the first and second detection portions further comprise a protective layer to prevent corrosion due to the liquid.

27. The sensor of claim 26, wherein the protective layer comprises a layer of gold and a layer of nickel.

28. A humidity detection system to detect a liquid content in a gas, comprising:
a current source to provide a current;
a board;
a first electrode disposed on said board and which receives the current;
a second electrode disposed on said board opposite said first electrode to form a gap therebetween into which the gas is received; and
a detection unit in communication with said second electrode to detect an amount of resistance across the gap,
wherein:
the amount of resistance corresponds to an amount of the liquid in the gas received in the gap,
a bottom surface of the gap exposed to the gas comprises a non-conductive material so as to prevent an electrical pathway from being established on the board between the first and second electrodes across the gap, and
said board comprises vents through which portions of the gas not received within the air pass.

29. The humidity detection system of claim 28, wherein said current source and said detection unit comprise a humidity detector.

30. The humidity detection system of claim 28, wherein said board comprises the non-conductive material and forms the bottom surface of the gap.

31. The humidity detection system of claim 30, wherein said board further comprises vents through which portions of the gas not received in the gap pass.

32. The humidity detection system of claim 30, wherein said board comprises a printed circuit board.

33. A humidity detection system to detect a liquid content in a gas, comprising:
a current source to provide a current;
a board;
a first electrode disposed on said board and which receives the current;
a second electrode disposed on said board opposite said first electrode to form a gap therebetween into which the gas is received; and
a detection unit in communication with said second electrode to detect an amount of resistance across the gap,
wherein:
the amount of resistance corresponds to an amount of the liquid in the gas received in the gap, and
said current source is a separate unit from said detection unit.

34. A humidity detection system to detect a liquid content in a gas, comprising:
a current source to provide a current;
a board;
a first electrode disposed on said board and which receives the current;
a second electrode disposed on said board opposite said first electrode to form a gap therebetween into which the gas is received;
a detection unit in communication with said second electrode to detect an amount of resistance across the gap; and
a resistor and a capacitor connected in parallel between a ground and said second electrode,
wherein the amount of resistance corresponds to an amount of the liquid in the gas received in the gap.

35. The humidity detection system of claim 34, wherein said resistor has a resistance according to an amount of voltage of said current source.

36. The humidity detection system of claim 34, wherein said board comprises vents through portions of the gas pass.

37. The humidity detection system of claim 36, wherein the portions of the pass which pass through the vents are the portions of the gas not received within the gap.

38. A humidity detection system to detect a liquid content in a gas, comprising:
a current source to provide a current;
a board having a vent;
a first electrode disposed on said board and which receives the current;
a second electrode disposed on said board opposite said first electrode to form a gap therebetween into which the gas is received; and
a detection unit in communication with said second electrode to detect an amount of resistance across the gap,
wherein:
the amount of resistance corresponds to an amount of the liquid in the gas received in the gap, and
portions of the gas pass through the vent.

* * * * *

UNITED STATES PATENT AND TRADEMARK OFFICE
CERTIFICATE OF CORRECTION

PATENT NO. : 6,835,920 B2
DATED : December 28, 2004
INVENTOR(S) : Jong-Chull Shon It is certified that error appears in the above-identified patent and that said Letters Patent is hereby corrected as shown below:

<u>Title page,</u>
Item [57], ABSTRACT,
Line 7, "space" should be -- spaced --.

<u>Column 8,</u>
Line 20, change "nonconductive" to -- non-conductive --.
Line 67, "there between" should be -- therebetween --.

<u>Column 9,</u>
Line 62, change "air" to -- gap --.

Signed and Sealed this

Twelfth Day of July, 2005

JON W. DUDAS
*Director of the United States Patent and Trademark Office*